United States Patent
Kindiger

(10) Patent No.: US 10,813,323 B1
(45) Date of Patent: Oct. 27, 2020

(54) **HEXAPLOID *SCHEDONORUS ARUNDINACEUS* PLANT THAT POSSESSES A *LOLIUM* MULTIFLORUM CYTOPLASM USEFUL FOR PRODUCING RHIZOMATOUS HYBRIDS**

(71) Applicant: The United States of America, as Represented by the Secretary of Agriculture, Washington, DC (US)

(72) Inventor: Bryan K. Kindiger, El Reno, OK (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/510,321

(22) Filed: Jul. 12, 2019

(51) Int. Cl.
*A01H 6/46* (2018.01)
*A01H 5/10* (2018.01)

(52) U.S. Cl.
CPC ............... *A01H 6/463* (2018.05); *A01H 5/10* (2013.01)

(58) Field of Classification Search
CPC .................................................... A01H 6/4618
See application file for complete search history.

(56) References Cited

PUBLICATIONS

Saxena et al Crop Science vol. 54, pp. 1205-121210 (Year: 2014).*

* cited by examiner

*Primary Examiner* — David H Kruse
(74) *Attorney, Agent, or Firm* — John Fado; Ariel Atkinson

(57) ABSTRACT

The tall *fescue* DH66OP Accession No. PI 690020 represents a genetic stock possessing an *L. multiflorum* cytoplasm that can enhance or induce rhizome formation across various genotypes. DH66OP may allow for the transfer the *L. multiflorum* cytoplasm to additional tall *fescue* genotypes for the recovery of genotypes expressing rhizomes.

5 Claims, No Drawings

HEXAPLOID *SCHEDONORUS ARUNDINACEUS* PLANT THAT POSSESSES A *LOLIUM* MULTIFLORUM CYTOPLASM USEFUL FOR PRODUCING RHIZOMATOUS HYBRIDS

BACKGROUND

Within the *Festuca-Lolium* genomic complex, there is a need for the rapid development of improved germplasm resources. Tall *fescue* [*Lolium arundinaceum*, (Schreb.) Darbysh./*Schedonorus arundinaceus* (Schreb.) Dumort., nom. cons.] represents a highly utilized, cool-season, perennial turf and forage species. Tall *fescue* generally exhibit a bunch grass phenotype that generally produces erect tillers that remain in close proximity to the plant base. Rhizomatous forms of tall *fescue* are known (such as those known as "Mediterranean" tall *fescue*) but the genetics, expression, and transmission of the trait appears complex at best and unknown at worst.

Rhizomatous forms of any grass turf or forage are highly desirable since the rhizomes represent rapidly spreading tillers that can fill voids in turf or pastures without the need for reseeding.

It is further desirable to identify novel genetic resources that can enhance traditional breeding methods and facilitate the development of improved *L. arundinaceum* germplasm for forage or turf production.

Cytoplasmic genomes found in plants contain the both mitochondrial and chloroplast genomes. Genes within the mitochondrial and chloroplast are known to have unique and often profound effects on nuclear gene expression. This interaction is often called nucleo-cytoplasmic interactions. Cytoplasm which involves the inheritance, transfer and genetic interaction with nuclear expressed gene systems have been well documented and through breeding, can have advantageous or disadvantages effects on the individual plant. One well known nucleo-cytoplasmic interaction is cytoplasmic male sterility (cms), where total or partial pollen sterility is the result of specific nuclear and mitochondrial genome interactions (Zhu and Weir. 1994. TAG 89:153-159). Another example is the conferring of various disease resistances or susceptibility in wheat, corn and other species (Shao, Shang, Hong and Liu. Frontiers in Microbiology 2016 7:1565). Effect of nuclear and cytoplasmic gene interactions are also known to have effects on plant fitness and adaptation (Laura F. Galloway and Charles B. Fenster, Evolution 53:1734-1743).

All of the references cited herein, including U.S. Patents and U.S. Patent Application Publications, are incorporated by reference in their entirety.

Mention of trade names or commercial products in this publication is solely for the purpose of providing specific information and does not imply recommendation or endorsement by the U.S. Department of Agriculture.

SUMMARY

The tall *fescue* DH66OP Accession No. PI 690020 represents a genetic stock possessing an *L. multiflorum* cytoplasm that can enhance or induce rhizome formation across various genotypes. DH66OP may allow for the transfer of a novel *L. multiflorum* cytoplasm to additional tall *fescue* genotypes for the recovery of genotypes expressing rhizomes. In particular, to produce rhizomatous plant materials or hybrids, DH66OP may be used as the maternal parent in a hybridization with another plant, such as a *Fescue* sp. or *Lolium* sp. plant.

Statement Regarding Deposit of Biological Material Under the Terms of the Budapest Treaty The inventor deposited 2500 seeds of DH66OP (*Lolium arundinaceum*/Schedonorus arundinaceus (Schreb.) Dumort., nom. cons.) as described herein on or before Apr. 5, 2019 with the American Type Culture Collection (10801 University Blvd. Manassas, Va. 20110-2209 USA), in a manner affording permanence of the deposit and ready accessibility thereto by the public if a patent is granted. The deposit has been made under the terms of the Budapest Treaty and the regulations thereunder. The deposit's accession number is PI 690020.

All restrictions on the availability to the public of DH66OP Accession No. PI 690020 which has been deposited as described herein will be irrevocably removed upon the granting of a patent covering this particular biological material.

The DH66OP Accession No. PI 690020 has been deposited under conditions such that access to the biological material is available during the pendency of the patent application to one determined by the Commissioner to be entitled thereto under 37 C.F.R. § 1.14 and 35 U.S.C § 122.

The deposited biological material will be maintained with all the care necessary to keep them viable and uncontaminated for a period of at least five years after the most recent request for the furnishing of a sample of the deposited microorganisms, and in any case, for a period of at least thirty (30) years after the date of deposit or for the enforceable life of the patent, whichever period is longer.

We, the inventors for the invention described in this patent application, hereby declare further that all statements regarding this Deposit of the Biological Material made on information and belief are believed to be true and that all statements made on information and belief are believed to be true, and further that these statements are made with knowledge that willful false statements and the like so made are punishable by fine or imprisonment, or both, under section 1001 of Title 18 of the United States Code and that such willful false statements may jeopardize the validity of the instant patent application or any patent issuing thereon.

DETAILED DESCRIPTION

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description discussion of several terms used herein follows.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 30%, preferably by as much as 20%, and more preferably by as much as 10% to a reference quantity, level, value, or amount. Although any methods and materials similar or equivalent to those described herein can be used in the practice or testing of the present invention, the preferred methods and materials are now described.

The amounts, percentages, and ranges disclosed herein are not meant to be limiting, and increments between the recited amounts, percentages, and ranges are specifically envisioned as part of the invention.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein).

The invention illustratively disclosed herein suitably may be practiced in the absence of any element (e.g., method (or process) steps or composition components) which is not specifically disclosed herein.

According to at least one exemplary embodiment, DH66OP Accession No. PI 690020 represents a genetic stock possessing an *L. multiflorum* cytoplasm that can enhance or induce rhizome formation across various *Festuca* (tall *fescue*) or *Lolium* sp. genotypes. DH66OP may allow for the transfer the *L. multiflorum* cytoplasm to additional tall *fescue* or *Lolium* sp. genotypes and the recovery of genotypes expressing rhizomes. Without being limited to specific examples, the maintenance of DH66OP can be accomplished through the sibbing of individuals as tall *fescue* is generally considered a self-incompatible species.

The material has been characterized for proprietary protection by possessing a specific *L. multiflorum* cytoplasm that is characterized by a series of Cp (chloroplast) based "TEA" molecular markers (data not shown). The particular DNA fingerprint, characterized by a series of "TEA" markers, distinguishes and characterizes the unique DNA profile of this novel cytoplasm.

Development of DH66OP Accession No. PI 690020

DH66OP was created by allowing a dihaploid (DH) recovery from a previous cross, DH66, to cross-pollinate with a wide array of tall *fescue* materials in a field nursery in 2012. DH66 was originally generated by hybridizing the DH inducing line IL3 with Nanyro tall *fescue*. The DH inducer line IL3 has not been previously described, but is similar to the IL1 line, which has been previously described (Kindiger, Notification of the Release of Annual Ryegrass Genetic Stock IL1, *J. of Plant Reg.* 6:117-120, 2012). Nanyro tall *fescue* is a non-rhizomatous, endophyte free cultivar release (Kindiger et al., Registration of Nanyro Tall *Fescue*, *Crop Sci*. 46:1815-1816, 2006). Following prior published methods regarding DH tall *fescue* production (Kindiger, sampling the Genetic Diversity of Tall *Fescue*, in: *Genetic Diversity in Plants*, Mahmut Caliskan (ed.), InTech, DOI: 10.5772/33273, 2012; Kindiger, Generation of Paternal Dihaploids in Tall *fescue*, *Grassland Sci*. 62:243-247, 2016) DH66 was generated. Briefly, pollen taken from Nanyro was used to pollinate the stigma of the IL3 inducer line; F1 hybrids were produced. F1 were kept in pollen isolation and at maturity, inflorescence from the F1 were harvested, dried, ground by hand and sown to germinating trays. From these germinations, tall *fescue* (cv. Nanyro) DH recoveries were produced and identified. One of these DH recoveries was assigned the code DH66.

DH66 was allowed to grow to maturity and allowed to cross-pollinate with numerous tall *fescue* genotypes in a field nursery in 2012 forming a DH66OP population. Seed of DH66OP were sown to the nursery in spring of 2014 where counts on the number of offspring exhibiting rhizomes were determined. With the exception of producing rhizomes and possession of the IL3 *L. multiflorum* cytoplasm, DH66OP is indistinguishable from other continental type, hexaploid tall *fescue* germplasm resources.

Characteristics of DH66OP Accession No. PI 690020

DH66OP represents a continental type hexaploid (2n=6x=42) tall *fescue* population that possesses a *L. multiflorum* cytoplasm that induces or enhances rhizome formation in tall *fescue*.

DH66OP can be used as a broad based, tall *fescue* genetic resource for selection within or backcrossing with superior tall *fescue* or *Lolium* sp. genotypes. The advantage to this rhizome induction approach is that rhizome formation can be induced across numerous genotypes that exhibit no prior rhizome development. The rhizome trait can be transferred in a single generation of hybridization by utilizing DH66OP as the maternal parent. It is important to note that rhizome formation in the hybrids can reveal itself in the first backcross generation. In addition, the generation of tall *fescue* recoveries not exhibiting rhizomes, but possessing the same *L. multiflorum* cytoplasm suggests a negative nuclear-cytoplasm interaction for rhizome formation. It should be noted that though the parental tall *fescue* genotype or cultivar may not possess rhizomes, this does not preclude the possibility that the paternal genotype utilized in the hybridization may have the potential to produce rhizomes in an appropriate cytoplasmic background.

In 2014, seed of DH66OP was sown to the field nursery for future selection and evaluation. In 2016, surviving plants in the nursery were counted and the frequency of offspring exhibiting rhizome formation of any length or number were obtained. Of the 132 surviving plants in the nursery, 73 exhibited varying degrees of rhizome formation. A similar approach was utilized to produce the rhizomatous-forming tall *fescue* cultivar cv. Armory (Kindiger, U.S. PVPO, PVP #201500219, Armory Tall *Fescue*, 2017). Without being limited by theory, the identification of individuals possessing no rhizome formation indicates strongly that there are tall *fescue* nuclear gene interactions that need to be present for the *L. multiflorum* cytoplasm to enhance or induce rhizome formation.

To produce rhizomes in such *Fescue* species/genotypes previously lacking rhizomes, the breeder needs to utilize the DH66OP line as the female parent in the hybridization with another *Fescue* or *Lolium* parent plant. By utilizing the DH66OP line as the maternal parent, the *Lolium* multiflorum cytoplasm conferring the rhizomatous trait is transferred to all offspring. In addition, an advantage of the use of this cytoplasm is that it is free of the toxic endophyte *Epichloë coenophiala* that produces alkaloids that are harmful to grazing livestock. In fact, the cytoplasm is free of any endophytes, toxic or otherwise. All materials generated from a breeding program utilizing DH66OP for the retention of the *Lolium* cytoplasm will be endophyte free.

The foregoing description and accompanying figures illustrate the principles, preferred embodiments and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A hexaploid *Schedonorus arundinaceus* (Schreb.) Dumort., nom. cons. (tall *fescue*) plant having accession number ATCC PI 690020, or a part thereof,
   wherein said hexaploid *Schedonorus arundinaceus* plant is capable of inducing rhizome formation in a child hybrid when used as the maternal parent in a hybridization with a paternal parent, and
   wherein said paternal parent does not possess rhizomes.

2. The hexaploid, *Schedonorus arundinaceus* plant or part thereof of claim 1, wherein said plant possesses a *Lolium multiflorum* cytoplasm.

3. A method of inducing rhizome formation in a hybrid plant, the method comprising:
   providing a maternal parent plant;
   providing a paternal parent plant; and
   crossing said maternal parent plant with said paternal parent plant to generate a hybrid plant,
   wherein said maternal parent plant is the hexaploid *Schedonorus arundinaceus* of claim 1,
   wherein said paternal parent plant does not possess rhizomes, and
   wherein said hybrid plant possesses rhizomes.

4. The method of claim 3, wherein said paternal parent plant is a *Fescue* or *Lolium* plant.

5. A hybrid plant produced by the method of claim 3.

* * * * *